United States Patent [19]

Lukasavage et al.

[11] Patent Number: 5,120,887
[45] Date of Patent: Jun. 9, 1992

[54] PROCESS OF MAKING PURE SOLEX

[75] Inventors: William Lukasavage, Succasunna; Steven Nicolich, Saddlebrook; Jack Alster, Fair Lawn, all of N.J.

[73] Assignee: The United States of America as represented by the Secretary of the Army, Washington, D.C.

[21] Appl. No.: 775,406

[22] Filed: Oct. 15, 1991

[51] Int. Cl.$^5$ .......................................... C07D 257/06
[52] U.S. Cl. ........................................ 568/924; 149/92; 149/105; 149/106; 540/475
[58] Field of Search ..................... 149/105, 106, 92; 568/924; 540/475

[56] References Cited

U.S. PATENT DOCUMENTS

| | | | |
|---|---|---|---|
| 3,415,868 | 12/1968 | Smetana et al. | 568/924 |
| 3,939,148 | 2/1976 | Siele et al. | 540/475 X |
| 4,432,902 | 2/1984 | McGuire et al. | 540/475 |
| 4,534,895 | 8/1985 | Frankel et al. | 540/475 |
| 4,614,800 | 9/1986 | Willer et al. | 540/475 X |
| 4,920,859 | 4/1989 | Millar et al. | 558/483 |

Primary Examiner—John S. Maples
Assistant Examiner—C. Sayala
Attorney, Agent, or Firm—Anthony T. Lane; Edward Goldberg; Edward F. Costigan

[57] ABSTRACT 1-(n)-acetyl-3,5,7-trinitrocyclotetramethylenetetramine is prepared by nitrolysis of 1,3,5,7-tetracyl-1,3,5,7-tetraazacyclooctane with a solution of nitric acid and nitrogen pentoxide or phosphorous pentoxide.

4 Claims, No Drawings

PROCESS OF MAKING PURE SOLEX

GOVERNMENTAL INTEREST

The Government has rights in this invention pursuant to Contract No. DAAA21-86-C-0171 awarded by Department of the Army.

The invention described herein was made in the course of or under a contract or subcontract thereunder with the Government and may be manufactured, used and licensed by or for the Government for Governmental purposes without the payment to us of any royalties thereon.

FIELD OF USE

This is a novel process for the direct making of 1-(n)-acetyl-3,5,7-trinitrocyclotetramethylenetetramine.

BACKGROUND OF THE INVENTION

SOLEX, otherwise known as 1-(n)-acetyl-3,5,7-trinitrocyclotetramethylenetetramine is a normal contaminant which appears in HMX. SOLEX has been known since the early industrial history of nitramine explosives. Due to its presence as a diluent in the purity of the desired product, it has been viewed as a nuisance.

Most research has been directed at hydrolyzing and/or extracting it from synthesized nitramines. Until the present process, no meaningful effort had been made to develop a direct synthesis of SOLEX. Recently this lack of synthetic knowledge of this compound has become a disadvantage.

The use of energetic burn rate modifiers for propellants has recently been the focus of attention and SOLEX has many of the attributes necessary as a useful modifier.

SUMMARY OF THE INVENTION

An object of the present invention is to provide a practical and cost effective process for producing SOLEX by nitrolysis of TAT otherwise known as 1,3,5,7-tetraacetyl-1,3,5,7-tetraazacyclooctane. Other objects will become apparent from the following description of the invention.

We have now discovered that SOLEX can be obtained at or near room temperature, in near quantitative yield, and at 99+% purity by reacting TAT with 98% nitric acid containing a small amount of phosphorous pentoxide. The resulting product is obtained pure by simply pouring the reaction mixture into water and filtering off the crystals. The resulting pure compound is useful, for burn rate modification of HMX bearing propellants.

Other outstanding features of this process are, viz. it produces a product which is essentially 100% pure in a quantitative yield that is essentially 100% pure. There are no by-products and therefore no resulting environmental problems. Further, it is essentially an isothermal room temperature reaction therefore requires no heating or cooling, to maintain or complete the reaction therefore, there are no utility costs. Further, since the reaction produces no exothermic heat, overheating is not and cannot be a problem. Overall, the process is both quick and efficient both quantitatively and qualitatively.

There are no excessive amount of reagents required, necessary, or desirable to maintain or complete the process. Further, the mild temperatures under which this synthesis takes place, do not create an unduly hostile environment for the substance. The process is carried out at room temperature.

The nitrogen pentoxide may be introduced as itself in the reaction mixture, or it may be gemerated in situ by ordinary scientific methods known in the art. To be more specific, the latter can be accomplished by employing a mixture of nitric acid, with a substance which is capable of reacting with nitric acid, under the conditions employed, to produce nitrogen pentoxide.

The process of the present invention is considered outstanding in view of the fact that the in prior art that SOLEX is a contaminant of HMX which is a nuisance even though only present in small amounts. The meager few percent of SOLEX present must also be painstakingly isolated to produce a useable product.

DESCRIPTION OF THE PREFERRED EMBODIMENTS

The following examples illustrate specific embodiments of the method of carrying out the process of the present invention. It is to be understood that they are illustrative only and do not in any way limit the invention.

EXAMPLE 1

Nitration of TAT with a Mixture of Nitric Acid and Phosphorous Pentoxide

A solution was prepared containing 75 grams of nitric acid and 13 grams of phosphorous pentoxide. The room temperature solution was poured into an empty 250 ml. beaker provided with a magnetic stirring bar, thermometer, and a watch glass was placed on top as a cover. With the stirrer running, 10 grams of TAT were cautiously added over a time internal sequence of about a 5 minute period. The temperature rose a few degrees Centigrade, but otherwise there was not an exotherm. The solution was allowed to stir, covered, at room temperature. Every 15 minutes, a drop of the solution was removed and dropped into a sample of water. This was to see if any water insoluble products had formed. After about 1½ to 2 hours at room temperature, a precipitate of water insoluble substance was detected. The reaction medium continued to become more and more dense with the product, SOLEX, until it continued to precipitate out of the reaction solution. After 5 to 6 hours, at room temperature, the mixture will generally become too thick to stir magnetically, and at about this time the reaction was complete. At this point, the entire mass was added, with rapid stirring, into about 5 times its mass of cool water. The precipitated product was filtered off as shiny needle shaped crystals. The purity, after rinsing with water, was found to be 99+% pure and the yield of the product, SOLEX, was found to be about 95 to 100%. However, this depends largely upon the purity of TAT employed. Analytical data to confirm our findings was obtained by HPLC, IR, and melting point.

EXAMPLE 2

The same proportions and methods were employed as set forth in Example 1. However, in this case, the temperature was elevated, and held constant at 30 degrees Centigrade. The presence of SOLEX was detected by a drop test between 1 to 1+½ hours after the TAT was completely dissolved. The reaction will generally be complete within 4 to 5 hours. The reaction will become too viscous to stir magnetically. The purity of the product obtained by this procedure, after rinsing with water, was about 99+% and the product-yield obtained was about 95 to 100%, depending largely upon the purity of TAT employed.

EXAMPLE 3

The same proportions and methods were employed as set forth in Example 1. However, in this embodiment, the temperature was elevated, and held constant at 40 to 45 degrees Centigrade. Water insoluble products were detectable within 45 minutes. At this temperature, the entire reaction will be complete within a 3 to 4 hour time frame. At this higher temperature, the product was found to have greater solubility, and it was stirable. However, the purity of the product was only found to be about 85 to 90%. However, at this temperature, the total product-yield, water rinsed and dried, was not greater than about 90%.

EXAMPLE 4

The same proportions and methods were followed again. However, the phosphorous pentoxide was replaced by nitrogen pentoxide. For the nitrogen pentoxide, we used two separate sources known to the scientific art. The first source of nitrogen pentoxide was derived by ozone treatment of dinitogen tetraoxide. The second source of the nitrogen pentoxide was derived from an electrolytic cell. In both cases, the results were similar to those obtained using phosphorous pentoxide.

EXAMPLE 5

The same proportions were employed as in Example 1. However, in this case, the reaction was run in a continuous mode at room temperature. In sequence, ⅓ of the reaction medium was removed after 30 minutes when the first positive detection of insoluble product was made. This sample was set aside to further age for 3 hours before work-up. After removing this sample, additional TAT and nitric acid, which contained the amount of phosphorous pentoxide required, was added. This was done to replace the volume of the reaction medium which had been removed. Samples were then taken every 90 minutes, until a total of 4 samples had been taken, and each sample was set aside for aging. The remaining reaction medium was allowed to sit for an additional 3 hours and worked up. All the samples were combined, filtered, rinsed with hot water and dried. The overall product-yield obtained was found to be about 83+%, and the purity of the product was above 95%.

CONCLUSION

As is known in the art, SOLEX, in pure form, is useful in that it can be converted to HMX by simple known techniques. It would prove to be a valuable starting reactant for large scale HMX production. To the inventor's knowledge, this is the only procedure in existence for the direct synthesis of SOLEX. This synthesis gives a 100% yield free of unwanted contaminants. It requires less than 3 moles of dinitogen pentoxide or its synthetic equivalent.

The process is a room temperature process and there is no requirement for heating or cooling. It is best practiced in a temperature range of between about 20° C. and 45° C. The process permits the instant isolation of the pure product by merely a precipitation with water. Therefor, no multiple recrystallizations are required.

In summary, it is an economical precursor for the industrial prepration of HMX. Also, it is known that SOLEX, in pure form, can be converted to HMX by simple treatment in strong nitric acid and may prove to be a valuable starting reactant for large scale HMX production.

The foregoing disclosure is merely illustrative of the principles of this invention and are not interpreted in a limiting sense. We wish it to be understood that we do not desire to be limited to the exact details described for obvious modifications will occur to a person skilled in the art.

What is claimed is:

1. In an improved process of making 1-(n)-acetyl-3,5,7-trinitrocyclotetramethylenetetramine by reacting 1,3,5,7-tetraazacycloctane with nitric acid and pentoxide of either nitrogen or phosphorous, the improvement comprising maintaining the reaction temperature up to about 45 degrees Centigrade for up to 6 hours at a nitric acid concentration ratio of greater than 7.5 to 1 based on said 1-(n)-acetyl-3,5,7-trinitrocyclotetramethylenetetramine to produce a product in near quantitative yield which is an essentially 100% pure.

2. The process according to claim 1, wherein the nitrogen pentoxide is employed.

3. The process according to claim 2, wherein the nitrogen pentoxide is formed in situ from a mixture of nitric acid and phosphorous pentoxide.

4. The process of claim 3 wherein the temperature is maintained at 20° C. and 25° for 16 hours.

* * * * *